United States Patent [19]

Strong

[11] Patent Number: 4,613,701

[45] Date of Patent: Sep. 23, 1986

[54] RECOVERY OF RHODIUM FROM HYDROFORMYLATION REACTION PRODUCT

[75] Inventor: James R. Strong, Bay City, Tex.

[73] Assignee: Celanese Corporation, New York, N.Y.

[21] Appl. No.: 777,648

[22] Filed: Sep. 19, 1985

[51] Int. Cl.$^4$ .............................................. C07C 45/50
[52] U.S. Cl. .................................... 568/454; 203/62; 203/87
[58] Field of Search .................... 568/454; 203/62, 87

[56] References Cited

U.S. PATENT DOCUMENTS

| | | | |
|---|---|---|---|
| 3,239,566 | 3/1966 | Slaugh | 568/454 |
| 3,527,809 | 9/1970 | Pruett | 568/454 |
| 4,148,830 | 4/1979 | Pruett et al. | 568/454 |
| 4,151,209 | 4/1979 | Paul et al. | 568/454 |
| 4,247,487 | 1/1981 | Brewester et al. | 568/454 |
| 4,275,243 | 6/1981 | Saito et al. | 568/454 |
| 4,287,369 | 9/1981 | Harris et al. | 568/454 |
| 4,479,012 | 10/1984 | Fisher et al. | 568/454 |
| 4,480,138 | 10/1984 | Hackman et al. | 568/454 |

*Primary Examiner*—Werren B. Lone
*Attorney, Agent, or Firm*—R. M. Pritchett

[57] ABSTRACT

In a hydroformylation process wherein an alpha-alkene of 2 to about 10 carbon atoms is reacted with carbon monoxide and hydrogen in the presence of a rhodium triorganophosphine complex to produce an aldehyde having one carbon atom more than the alkene, the aldehyde product being continuously separated from the liquid reaction medium by gas stripping or distillation, rhodium moiety is recovered from the condensed reactor overhead vapors by redistillation under defined conditions.

6 Claims, No Drawings

RECOVERY OF RHODIUM FROM HYDROFORMYLATION REACTION PRODUCT

BACKGROUND OF THE INVENTION AND RELEVANT PRIOR ART

This invention relates to the hydroformylation of a lower alkene to produce an aldehyde having one carbon atom more than the alkene feedstock by a process which comprises reacting a mixture of hydrogen and carbon monoxide with the alkene in the presence of a catalyst which comprises rhodium complexed with a triorganophosphine as exemplified by triphenylphosphine, which is particularly useful and with which the present invention is primarily concerned. Hydrogen and carbon monoxide also make up part of the complexed rhodium catalyst. The reaction is conducted in the presence of a liquid reaction medium comprising a high-boiling solvent.

The invention is specifically directed to those reaction systems, which are well known in the pertinent prior art, in which the hydrogen, carbon monoxide, and vapors of the alkene are sparged through the liquid reaction medium during the course of the reaction both to effect agitation of the reaction medium and also to strip out the aldehyde product as it is formed, in the vaporous mixture exiting the hydroformylation reactor.

The literature dealing with hydroformylation reaction systems of the type just described is voluminous. U.S. Pat. No. 3,527,809, to Pruett et al., provides a comprehensive discussion of the chemistry of these systems. U.S. Pat. No. 3,239,566, to Slaugh et al., is also pertinent as background for the basic process.

U.S. Pat. No. 4,151,209, to Paul et al., provides a discussion of product recovery by stripping of the liquid reaction medium and also discusses applicable high-boiling reaction solvents. U.S. Pat. No. 4,480,138, to Hackman et al., also discusses especially useful reaction solvents and deals at considerable length with the technology of the product-stripping operation itself.

U.S. Pat. No. 4,148,830, to Pruett et al., teaches the use of high-boiling reaction by-products as the reaction solvent.

The recovery of the aldehyde product from the liquid reaction medium can be effected in a number of ways including continuously drawing off a slip stream from the hydroformylation reactor and distilling it to separate relatively low-boiling compounds including the aldehyde product as an overhead stream and then returning the stripped residue to the hydroformylation reactor as desired. Alternatively, the continuous stripping of the reaction medium by sparging hydrogen, carbon monoxide, and alkene vapors into the liquid contained in the hydroformylation reactor, with the aldehyde product being continuously withdrawn from the top of the reactor in the exiting gases, is particularly useful when the aldehyde is of substantial volatility, as in the case of propionaldehyde and the butyraldehydes. The continuous hydroformylation of propylene in a gas-sparged reactor in this manner is discussed by Hershman et al. in "Industrial and Engineering Chemistry Product Research and Development," Vol. 8 (1969) pages 372-375.

Finally, U.S. Pat. No. 4,247,486, to Brewester et al., describes a system in which the gas recycle through the hydroformylation reactor is controlled in such a manner as to maintain the liquid level in the reactor and control the build-up of high molecular weight by-products.

The potential problem of loss of valuable rhodium in the reactor overhead in the form of entrainment is mentioned in U.S. Pat. No. 4,247,486, and also in U.S. Pat. No. 4,287,369, to Harris et al., who also describe a product-recovery system in which the gases exiting the hydroformylation reactor are subjected to condensation with non-condensed components being recycled to the hydroformylation reactor. Both U.S. Pat. No. 4,247,486 and U.S. Pat. No. 4,286,369 disclose the use of demisting pads through which the gases exiting the hydroformylation reactor are passed in order to remove entrained liquid droplets for return to the reactor. In neither case is there a suggestion that the demisting pads are in any way deficient in preventing loss of rhodium from the reaction system.

It has now been discovered. however, that conventional entrainment separators such as the demisting pads disclosed in the prior art just described are not completely effective in preventing loss of rhodium into the reactor overhead system. Even small losses of rhodium through the entrainment-separation system are very significant economically because of the high cost of rhodium. Also, of course, rhodium is a strategically-important metal regardless of its monetary cost. It is not known with certainty whether these losses of rhodium through the, for example, demisting pads occur as very fine entrainment which is not trapped by the pads or whether there is actually some volatilization of the rhodium as complexes which have an appreciable, although certainly very low, volatility.

It is, accordingly, an object of the present invention to provide a method for recovering that portion of the rhodium which exits the top of the hydroformylation reactor and which is not trapped by conventional demisting equipment. It is also another object to recover this fugitive rhodium substantially free from high-boiling reaction by-products which, if returned to the hydroformylation reactor, tend to act as catalyst deactivators. Other objects will be apparent from the following detailed description.

SUMMARY OF THE INVENTION

In accordance with the present invention the reaction condensate obtained by condensing the vapors which are stripped overhead with the aldehyde products in a hydroformylation reactor operating as previously described are condensed is redistilled to produce, first, a distillate comprising the aldehyde hydroformylation product along with a residue comprising substantially the entirety of those components of the hydroformylation product condensate which are less volatile than the aldehyde product. This residue is then redistilled to separate it into (a) a redistillation overhead stream which comprises substantially the entirety of those compounds present which are more volatile than the ligand which is used in the hydroformylation catalyst system (typically and normally triphenylphosphine) and (b) a redistillation residue which comprises those components of the initially-obtained hydroformylation reaction product condensate which are equal to or lower than the ligand (typically triphenylphosphine) in volatility and which include any rhodium moiety which may have been initially present in the condensed hydroformylation reaction product vapors. The rhodium-containing residue from the second distillation not only contains substantially the entirety of the rhodium which was initially lost out the top of the hydroformylation reactor, but it also is substantially free of high-boiling reaction by-products which tend to deactivate the hydroformylation catalyst as they build up in the hydroformylation reactor. Free of these compounds, the residue obtained from this second redistillation is suitable for recycle to the hydroformylation reactor as catalyst makeup.

DETAILED DESCRIPTION

The invention is not restricted in its applicability to hydroformylation reaction systems employing any particular reaction solvent, although it is especially useful in systems in which the reaction solvent is either a high-molecular weight polyalkylene glycol or else a high molecular weight alkane, including especially linear alkanes. If desired, it can also be employed with systems in which the hydroformylation reaction solvent comprises high molecular weight by-products of the hydroformylation reaction itself. Broadly speaking, the fundamental principle is also applicable to reaction systems, as known in the art, in which the aldehyde product is recovered by redistilling a slipstream drawn from the liquid contained in the hydroformylation reactor. That is, systems which use a liquid drawoff from the reactor rather than recovering the aldehyde product from vapors withdrawn from the head of the reactor. In this latter adaptation, the problem being addressed is not the escape of rhodium from the reactor in vapors which are withdrawn from its head. Rather, the problem is recovering the rhodium in condition fit for recycle to the hydroformylation reactor substantially free from catalyst deactivators which, it has been discovered, boil at a temperature slightly lower than the boiling point of the reaction ligand, (e.g., triphenylphosphine). In this particular embodiment care is taken to include a step in the series of distillations used to work up the crude reaction product wherein there is distilled overhead, and away from a rhodium-containing residue, a cut which boils just before the reaction ligand. Care is taken not to return this cut to the hydroformylation reaction system.

The invention is broadly applicable to systems in which any alkene, more particularly any alpha-alkene, having from 2 to about 10 carbon atoms is hydroformylated in accordance with the prior-art practices previously discussed hereinabove to produce an aldehyde having one carbon atom more than the alkene. It is particularly useful, however, in processes for converting ethylene to propionaldehyde and processes for converting propylene to butyraldehydes including especially n-butyraldehyde. As previously explained, these processes use a high-boiling liquid reaction solvent and a rhodium-complex catalyst wherein the ligand is typically a phosphine but especially triphenylphosphine. In particular the present invention is directed to that operating mode in which a gaseous mixture comprising carbon monoxide, hydrogen, and the alkene being hydroformylated is continuously bubbled through the liquid reaction medium containing the catalyst, with the aldehyde product, as it is formed, being continuously removed from the head of the reactor in a stream of the gas which has passed through the reaction medium. The gas is passed through the reaction medium at such a rate as to maintain a constant liquid level in the reactor. The total reactor pressure is normally about 5 to 40 atmospheres, and the reaction temperature is approximately 80° to 150° C. The concentration of rhodium in the liquid reaction medium is typically about 500 to 1400 ppm calculated as rhodium. The rate of gas reactor throughput is not critical to the purposes of the present invention, but typical industrial applications entail gas throughput rates such that the total volume of gases and vapors, including both fixed gases and condensable vapors, leaving the head of the hydroformylation reactor is about 0.5 to 7.5 volumes of total gases and vapors per minute (measured at reaction temperature and pressure) per volume of liquid contained in the hydroformylation reactor.

As previously mentioned, the prior art is not unacquainted with the fact that there is some danger of the entrainment of rhodium into the gases leaving the hydroformylation reactor. The present invention is based on the discovery that the problem is greater than previously realized. It is also based in part on the discovery that, over and above the rhodium-entrainment problem, there is also a catalyst deactivation problem associated with the buildup of high-boiling reaction by-products which are more volatile that the reaction ligand which is being employed but less volatile than the aldehyde product and the intermediate reaction by-products boiling just above the aldehyde.

Broadly speaking, the present invention comprises redistilling the crude product condensate formed by condensing the vapors drawn off from the head of the hydroformylation reactor to separate it into a light cut comprising the aldehyde product, a cut comprising compounds which are less volatile than the aldehyde product but more volatile than the reaction ligand (typically triphenylphosphine) and a final residue comprising those components of the original crude reaction product condensate which are equal to or lower than triphenylphosphine in volatility and which includes the rhodium. Although this can be accomplished if desired in an arrangement of continuously-operating distillation towers, it is convenient to recover the aldehyde and those compounds boiling close to it in a continuous primary distillation of the crude hydroformylation reaction product condensate, with the higher-boiling compounds remaining after the removal of the aldehyde being then worked up in a batch distillation. The initial distillation of the reaction product condensate to recover a distillate comprising the bulk of the aldehyde formed in the hydroformylation reaction entails obvious distillation techniques well known to those skilled in the art. Details of the present invention are largely concerned with the workup of the crude reaction heavy ends mixture which remains as a residue after the bulk of the aldehyde product has been distilled out of the initial crude reaction product condensate. That is, the present invention is concerned with working up the heavy ends remaining after the bulk of the aldehyde product has been separated for further purification by conventional methods which are known in the art. Some aldehyde typically remains in these heavy ends, of course, and can be recovered from them in the present process before further processing of the residues to remove deleterious high-boiling by-products and recover a final stripped residue which contains the rhodium and is suitable for recycle to the hydroformylation reactor.

Advantageously the present process is applied to the residue which remains after the hydroformylation reactor condensate product has been distilled to recover substantially the entirety of the aldehyde hydroformylation product and those compounds which are close to it in boiling point (e.g., the corresponding alcohol). As previously explained, distillation of the reaction product condensate to recover the aldehyde product involves known technology and is an inherent part of any hydroformylation process entailing removal of the product from the hydroformylation reactor in the vapor phase. The present invention is directed primarily to processing the residue which remains after the bulk of the aldehyde product has been separated.

The present rhodium-recovery system does not require careful fractionation and can be carried out in a simple flasher, although a few fractionation trays of a type adapted to very low pressure-drop operation will help in obtaining sharp separations. However, because the desired rhodium-containing residue product is so very low in volatility, a simple vacuum flash without trays is satisfactory and economical. There are, however, certain operating controls which should be maintained. First, for those stages of the distillation or evaporation in which butyraldehyde is present in the apparatus, temperatures above about 232° C. should be avoided because this is the auto-ignition point of butyraldehyde. Operation under vacuum can entail a leakage of air into the system, and butyraldehyde can ignite if temperatures are higher than 232° C. Higher temperatures up to about 260° C. can be employed in the substantial absence of butyraldehyde. Above 260° C. there is danger that deactivation of the rhodium catalyst in the stillpot may take place. Broadly, operating stillpot temperatures will be between 149° C. and 260° C., with temperatures between 205° C. and 232° C. being preferred. Operating pressure is preferably between about 10 mm HgA and 25 mm HgA in a "single-pass" mode of operation or in the second pass of a "two-pass" operation. In a two-pass operation, the initial pass is preferably operated at about 40–45 mm HgA. By "single-pass" operation is meant distilling overhead substantially everything boiling lower than the ligand (e.g., triphenylphosphine), with the resulting distillate being further processed as desired while the residue is suitable for recycle to the hydroformylation reactor. By "two-pass operation is meant operation in which relatively light compounds such as the aldehyde, the corresponding alcohol, the corresponding alkyl alkanoate (e.g., butyl butyrate when the aldehyde is butyraldehyde), and corresponding aldol derivatives (e.g., ethylhexanal and ethylhexenal when butyraldehyde is the aldehyde product) are taken overhead in a first pass, with higher-boiling heavy ends including a riser cut of the hydroformylation reaction solvent and also including some of the ligand being brought overhead in a second pass. In processing material derived from the hydroformylation of propylene to form butyraldehyde using a triphenylphosphine ligand and a polyalkylene glycol as reaction solvent, it is recommended that the 2-stage distillation system be so operated as to bring overhead in the first stage butyraldehyde, butanol, and heavy ends having atomospheric boiling points up to about 290° C., while in the second distillation stage heavy ends having atmospheric boiling points between about 290° C. and 384° C. are brought overhead. It is desirable to leave a substantial portion of the phosphine ligand in the residue. It will be understood that in the second stage the distillate which is brought overhead may include some of the high-boiling hydroformylation reaction solvent, but it is, of course, contemplated that the greater portion of such solvent which is present is to remain as undistilled residue.

Careful fractionation is not actually necessary in carrying out the process if the last flash stage is so conducted that the distillate contains an appreciable amount of phosphines (e.g. about 2% or more phosphines in the distillate). Temperature control can be by instruments sensing the pot temperature. All distillation temperatures discussed herein are stillpot temperatures.

EXAMPLE 1

Propylene was hydroformylated in a polyalkylene glycol reaction solvent. The catalyst comprised rhodium complexed with triphenylphosphine ligand. The product was continuously removed from the hydroformylation reactor in the vapor phase in a stream of gas comprising carbon monoxide, hydrogen, and propylene which was continuously bubbled through the liquid contained in the hydroformylation reactor and then removed from the top of the reactor carrying with it the butyraldehyde product in vapor form. The gases evolved from the top of the hydroformylation reactor were passed through a condenser to recover a crude hydroformylation reaction product condensate which was then redistilled to recover the bulk of the butyraldehyde for further processing outside the scope of the present invention. The residues remaining after removal of the butyraldehyde product were then further distilled to form a distillation residue which contained substantially the entirety of everything boiling above about 384° C. at atmospheric pressure which was initially contained in the crude hydroformylation reaction condensate. In particular, this heavy ends residue after butyraldehyde removal contained, in addition to minor amounts of butyraldehyde and butanol, substantial proportions of 2-ethylhexanal, 2-ethylhexenal, butyrates, triorganophosphines, and heavy ends including quantities of the hydroformylation reaction solvent. It also contained about 70 ppm of rhodium even though the gases leaving the hydroformylation reactor had been passed through about 4 feet of "Koch-Sulzer" (Koch Engineering Co.) mist-eliminating packing irrigated with liquid reflux at about 0.334 liters of liquid per square meter of packed cross-section per second.

The approximate analysis of this heavy ends residue was as follows:

Butyraldehydes—1%
Butanol—5%
2-Ethylhexanal—27%
2-Ethylhexenal—21%
Esters—18%
Propyldiphenylphosphine—2.5%
Propyldiphenylphosphine Oxide—0.2%
Triphenylphosphine—6%
Triphenylphosphine Oxide—1%
Rhodium—70 ppm The rhodium-containing residue just described was first flashed in a simple single-stage flasher with no trays at an average pot temperature of about 175° C. and operating at a pressure of approximately 40 mm HgA to distill overhead substantially the entirety of all the components initially present having boiling points lower than the phosphines that were present. There was a very small concentration of phosphine in the distillate, i.e., about 1.3 wt % calculated as triphenylphosphine.

After the initial flashing step just described, the same flash vessel was employed, at elevated temperature and lowered absolute pressure, to distill overhead a substantial portion of the phosphines and organic heavy ends which remained in the residue from the first flashing step just described. In the second step, which was also conducted batchwise, the evaporator was run to a final pot temperature of about 245° C. and at an absolute pressure of about 20 mm HgA. The distillate obtained in this second step contained, by weight, about 18 wt % phosphines calculated as triphenylphosphine and about 30 wt % organic heavy ends. The residue contained about 30 wt % phosphines and 65 wt % heavy ends as well as 1150 ppm of rhodium. The distillate from this step contained less than 1 ppm of rhodium.

Tests indicated that the residue could be recycled safely to the hydroformylation reactor over a period of time without causing appreciable buildup of catalyst deactivators.

The embodiments of the invention in which an exclusive property or privilege is claimed are:

1. In a process for hydroformylating an alkene of 2 to about 10 carbon atoms having a double bond in the alpha position by (a) reacting said alkene at about 80° C. to 150° C. with carbon monoxide and hydrogen in the presence of a liquid reaction medium containing as hydroformylation catalyst a complex of rhodium with triphenylphosphine and carbon monoxide to produce a liquid reaction mixture comprising triphenylphosphine, an aldehyde derivative of said alkene having one carbon atom more than said alkene, and reaction by-products; (b) stripping said liquid reaction mixture by gas stripping, distillation, or evaporation during the course of said hydroformylation reaction to remove overhead from said reaction mixture a vapor stream comprising said aldehyde derivative, (c) recovering a crude product condensate comprising said aldehyde derivative from said vapor stream, and (d) distilling the bulk of the aldehyde out of said condensate leaving behind a crude reaction heavy ends mixture, the improvement which comprises:

separating said crude reaction heavy ends mixture by distillation into an aldehyde product distillate comprising said aldehyde derivative and a first distillation residue comprising substantially the entirety of those components of said reaction heavy ends mixture which are less volatile than said aldehyde derivative; and redistilling said first distillation residue to separate said first distillation residue into (1) a redistillation overhead stream comprising those components of the crude reaction heavy ends mixture which are more volatile than triphenylphosphine and (2) a redistillation residue stream comprising those components of the crude reaction heavy ends mixture which are equal to or lower than triphenylphosphine in volatility and including any rhodium moiety initially contained in said vapor stream.

2. The improvement of claim 1 wherein said alkene is propylene and said aldehyde derivative is butyraldehyde.

3. The improvement of claim 2 wherein said distillation of said crude reaction heavy ends mixture comprises a first stage conducted under vacuum during which substantially all of the butyraldehyde in said reaction heavy ends mixture is brought overhead as distillate and during which the maximum temperature obtaining within the still is maintained below about 165° C.

4. The improvement of claim 3 wherein said distillation comprises two stages, the butyraldehyde, butanol, and heavy ends having atmospheric boiling points up to about 290° C. being brought overhead in the first stage and heavy ends having atmospheric boiling points between about 290° C. and 384° C. being brought overhead in the second stage.

5. The improvement of claim 4 wherein said liquid reaction medium comprises a high-boiling inert liquid solvent.

6. The improvement of claim 5 wherein said high-boiling solvent is a polyalkylene glycol.

* * * * *